United States Patent
Maegawa et al.

(10) Patent No.: US 7,060,963 B2
(45) Date of Patent: Jun. 13, 2006

(54) ORGANISM INFORMATION MEASURING DEVICE AND ORGANISM INFORMATION MEASURING METHOD

(75) Inventors: Kazuya Maegawa, Chiba (JP); Takashi Nakamura, Chiba (JP); Koichi Moriya, Chiba (JP); Shinichiro Miyahara, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 11/121,320

(22) Filed: May 3, 2005

(65) Prior Publication Data

US 2005/0253047 A1 Nov. 17, 2005

(30) Foreign Application Priority Data

May 17, 2004 (JP) .............................. 2004-146077

(51) Int. Cl.
 *A61B 5/02* (2006.01)
(52) U.S. Cl. ........................ 250/221; 600/323; 600/500
(58) Field of Classification Search ................ 250/221; 600/500, 502, 310, 323
See application file for complete search history.

(56) References Cited

U.S. PATENT DOCUMENTS 6,198,951 B1 * 3/2001 Kosuda et al. .............. 600/323

FOREIGN PATENT DOCUMENTS

JP 01078973 3/2001

* cited by examiner

*Primary Examiner*—Kevin Pyo
(74) *Attorney, Agent, or Firm*—Adams & Wilks

(57) ABSTRACT

An organism information measuring device has two light irradiating parts that irradiate light of short and long wavelength, respectively, toward an organism, and two light receiving parts that receive backward scattered light from the organism and produce organism information signals according to the quantity of received light. A data processor determines organism information indicative of a condition of the organism based on the organism information signals. The two light irradiating parts may be combined into a single light irradiating part, with one of the light receiving parts disposed farther from the light irradiating part than the other and having a light receiving area larger in size than that of the other and proportional to the distance thereof from the light irradiating part.

11 Claims, 7 Drawing Sheets

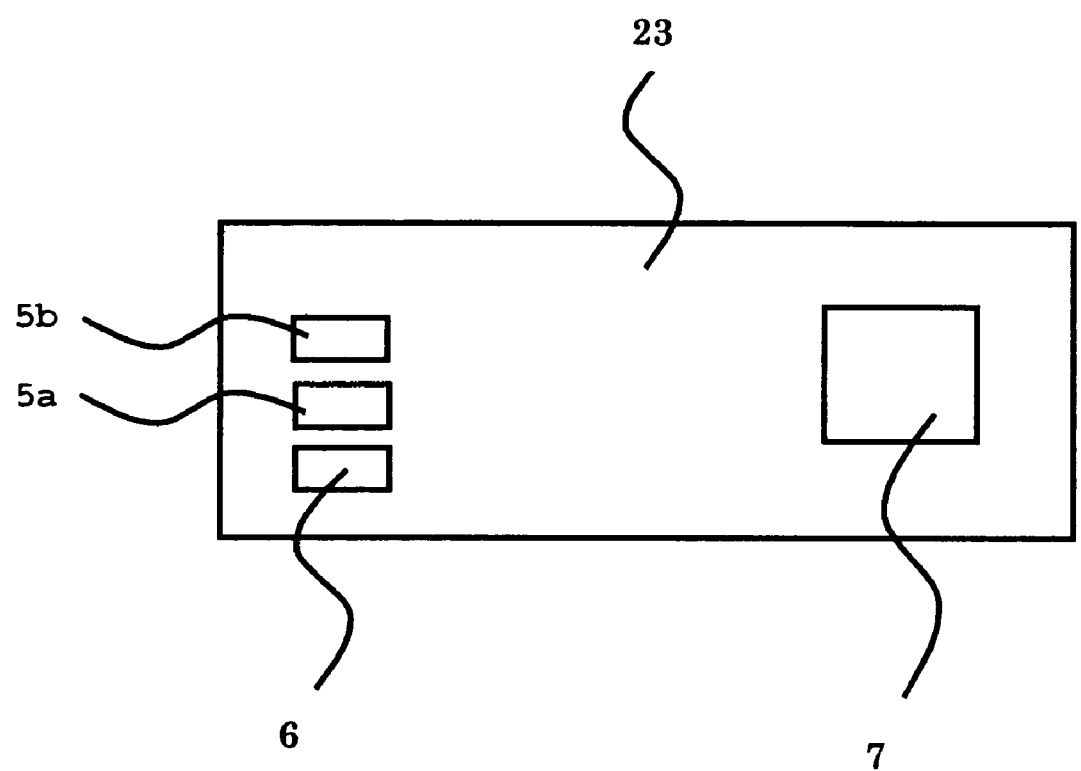

ORGANISM INFORMATION MEASURING DEVICE AND ORGANISM INFORMATION MEASURING METHOD

BACKGROUND OF THE INVENTION

1. Field of the Invention

The present invention relates to an organism information measuring device capable of measuring an organism information such as pulse rate under a state of being mounted to a wrist (arm), and an organism information measuring method.

2. Description of the Prior Art

Due to an increase in concern for health care in recent years, various kinds of organism information measuring devices, which can measure various organism information such as pulse rate while being mounted to the wrist (arm) and the like intact, have been proposed. See, for example, Japanese Published Patent Application No. 2001-078973 (Patent Document 1).

In the organism information measuring device described in Patent Document 1, under the state of being mounted to the wrist, a light is irradiated from an LED toward an organism. Backward scattered light from blood in a blood vessel is received by a photodiode, and the pulse rate is calculated by extracting a pulse signal from the backward scattered light. Especially, since a measurement of the pulse rate can be easily performed while being mounted to the wrist intact, it is simply used by a user.

By the way, in the organism information terminal device described in the above Patent Document 1, there has been a fear that, in addition to the fact that the light containing a pulse information is received when receiving the backward scattered light from the organism by the photodiode, there is received a light containing no pulse information, for example, a light directly entering from the LED, a light reflected by an organism surface, or a light reflected by a transparent glass disposed above the LED. By this, in the photodiode, a noise (electrical disturbance) increases, and a reduction in S/N ratio has occurred. Accordingly, there has been a possibility that an accurate organism information cannot be measured.

SUMMARY OF THE INVENTION

The present invention is one made in view of such circumstances, and its object is to provide an organism information measuring device and an organism information measuring method, in each of which it is possible to improve the S/N ratio and increase a measurement accuracy of the organism information.

In order to solve the above problems, the present invention provides means mentioned below.

An organism information measuring device of the present invention is one characterized by possessing a main body disposed under a state that its lower face has contacted with an organism surface, a light irradiating part which is disposed in the lower face of the main body and irradiates a light toward an organism, a 1st light receiving part which is disposed in the lower face of the main body and near the light irradiating part, receives a backward scattered light from the organism and generates an organism information signal complying with a received light quantity, a 2nd light receiving part which is disposed in the lower face of the main body and in a position spaced from the light irradiating part more than a distance between the 1st light receiving part and the light irradiating part, receives a backward scattered light from the organism and generates an organism information signal complying with a received light quantity, and an organism information operating part which calculates an organism information on the basis of the organism information signals having been generated by the 1st light receiving part and the 2nd light receiving part.

In this organism information measuring device concerning the invention, after the lower face of the main body has been contacted with the organism surface, a light is irradiated from the light irradiating part toward the organism. The irradiated light is absorbed and scattered in the organism by tissue, such as fat and muscle, and the blood, and one part of the irradiated light is received as the backward scattered light by the 1st light receiving part and the 2nd light receiving part. This received light fluctuates with a change in blood quantity by a pulsation. The 1st light receiving part and the 2nd light receiving part receive this backward scattered light and generate pulse signals (organism information signals) in accordance with a change in the received light quantity.

On this occasion, since the 1st light receiving part is disposed near the light irradiating part, it receives the light depending on the light irradiating part. That is, it receives the light containing no organism information. On the other hand, since the 2nd light receiving part is disposed in a position spaced farther from the light irradiating part than the 1st light receiving part, it receives the backward scattered light from the organism in addition to receiving the light depending on the light irradiating part.

On the basis of the organism information signal generated by the 1st light receiving part and the organism information signal generated by the 2nd light receiving part, i.e., by taking the organism information signal generated by the 1st light receiving part into consideration, the organism information operating part can remove as far as possible the light containing no organism information, i.e., noise (electrical disturbance), from the organism information signal generated by the 2nd light receiving part. By this, it is possible to improve S/N ratio, and it is possible to perform a more accurate calculation of the organism information.

Further, an organism information measuring device of the present invention is one characterized in that, in the above organism information measuring device of the present invention, the light irradiating part possesses a 1st light irradiating part for detecting a noise and a 2nd light irradiating part for detecting an organism information, each of which irradiates a light different in wavelength, and, between both the light irradiating parts, the 1st light irradiating part utilizes a light whose wavelength is short and the 2nd light irradiating part utilizes a light whose wavelength is long.

In this organism information measuring device concerning the invention, since it possesses the 1st light irradiating part and the 2nd light irradiating part, the 1st light receiving part receives much more light containing no organism information (much in noise component), and the 2nd light receiving part receives much more backward scattered light from the organism. Accordingly, it is possible to additionally improve S/N ratio, and it is possible to perform the more accurate calculation of the organism information. Especially, since the 2nd light irradiating part utilizes the light whose wavelength is long, it is easy to obtain the backward scattered light from the organism.

Further, an organism information measuring device of the present invention is one characterized in that, in the above organism information measuring device of the present invention, the 2nd light receiving part is disposed at a distance in which the light irradiated from the 1st light irradiating part does not directly enter.

In this organism information measuring device concerning the invention, since the 2nd light receiving part is disposed at the distance in which the light irradiated from the 1st light irradiating part does not directly enter, it collectively receives the backward scattered light without undergoing an influence from the 1st light irradiating part. Accordingly, it is possible to accurately calculate the organism information.

Further, an organism information measuring device of the present invention is one characterized in that, in any of the above organism information measuring devices of the present invention, the 2nd light receiving part is set such that a light receiving area increases in compliance with a distance spacing from the light irradiating part.

In this organism information measuring device concerning the invention, since the 2nd light receiving part is set such that the light receiving area increases in compliance with the distance spacing from the light irradiating part, it receives much more backward scattered light which has attenuated. By this, the 2nd light receiving part can increase the received light quantity.

Accordingly, the organism information operating part can more surely remove the light containing no organism information, i.e., noise component, and thus can more accurately perform the calculation of the organism information.

Further, an organism information measuring device of the present invention is one characterized in that, in any of the above organism information measuring devices of the present invention, the 1st light receiving part is provided in plural pieces, and the organism information operating part utilizes any one or an average value of the organism information signals having been generated by the plural 1st light receiving parts.

In this organism information measuring device concerning the invention, since it has the plural 1st light receiving parts, the light containing no organism information, i.e., a noise component, can be surely received irrespective of the position where the 1st light receiving part is disposed. And, by utilizing any one or the average value of the organism information signals having been generated by the plural 1st light receiving parts, the organism information operating part can additionally accurately perform the calculation of the organism information.

Further, an organism information measuring method concerning the present invention is an organism information measuring method in which a light is irradiated from a light irradiating part toward an organism, a backward scattered light from the organism is received in two places of a 1st light receiving part disposed near the light irradiating part and a 2nd light receiving part spaced from the light irradiating part more than a distance between the 1st light receiving part and the light irradiating part, and an organism information is measured on the basis of the results of received light of both the light receiving parts, characterized by possessing a transformation process in which, from the backward scattered light received by the 1st light receiving part and the 2nd light receiving part, organism information signals complying with a received light quantity are respectively generated and the organism information signals are high-speed-Fourier-transformation-processed, and an operation process in which values transformed by the transformation process are normalized by a power spectrum of optional frequency and the organism information is operated by mutually subtracting the normalized values.

In this organism information measuring method concerning the invention, the light irradiated from the light irradiating part toward the organism is absorbed and scattered in the organism by the tissue, such as fat and muscle, and the blood, and one part of the irradiated light is received as the backward scattered light by the 1st light receiving part and the 2nd light receiving part. This received light fluctuates with the change in blood quantity by the pulsation.

And, by the transformation process, the 1st light receiving part and the 2nd light receiving part receive this backward scattered light and generate pulse signals (organism information signals) complying with a change in the received light quantity, and the pulse signals are high-speed-Fourier-transformation-processed. On this occasion, since the 1st light receiving part is disposed near the light irradiating part, it receives more light depending on the light irradiating part. That is, it is receiving much light containing no organism information. On the other hand, since the 2nd light receiving part is disposed in the position spaced from the light irradiating part more than the 1st light receiving part, it is receiving more backward scattered light from the organism in addition to receiving the light depending on the light irradiating part.

And, by the operation process, by normalizing the high-speed-Fourier-transformation-processed values by the power spectrum of optional frequency and mutually subtracting the normalized values, it is possible to remove as far as possible the noise (electrical disturbance) from the organism information signal generated by the 2nd light receiving part.

Accordingly, it is possible to improve S/N ratio, and it is possible to perform the accurate calculation of the organism information.

BRIEF DESCRIPTION OF THE DRAWINGS

A preferred form of the present invention is illustrated in the accompanying drawings in which:

FIG. 9 is a view showing a positional relation between two LEDs and two PDs in a modified arrangement, as viewed from above a cover glass.

DETAILED DESCRIPTION OF THE PREFERRED EMBODIMENTS

Figure 1:
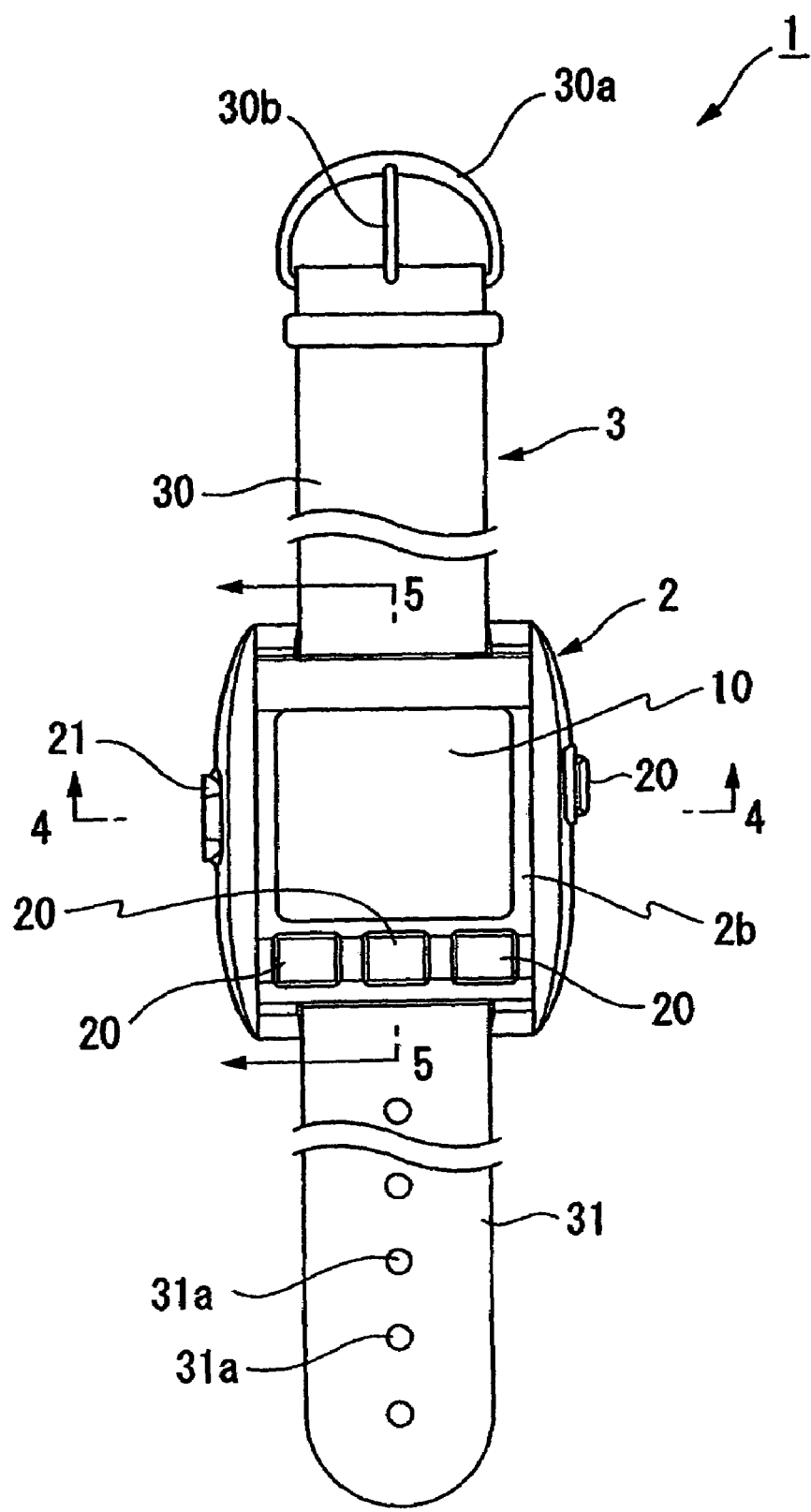
FIG. 1 is a front view showing one embodiment of an organism information measuring device concerning the present invention.

Hereunder, one embodiment of each of an organism information measuring device and an organism information measuring method, which concern the present invention, is explained by referring to FIG. 1 to FIG. 8.

As shown in FIG. 1 to FIG. 6, an organism information measuring device 1 of the present embodiment is a wristwatch type, and one calculating the pulse rate that is the organism information under the state of being mounted to a wrist (arm) A.

This organism information measuring device 1 accommodates therein various electrical components and electronic components, and comprises a housing (main body) 2 disposed under a state that its lower face 2a contacts with an organism surface B, and fixing means 3 which mounts the housing 2 to the wrist A. Further, a protrusion part 4 protruding from the lower face 2a is formed in the lower face 2a of the housing 2.

Figure 6:
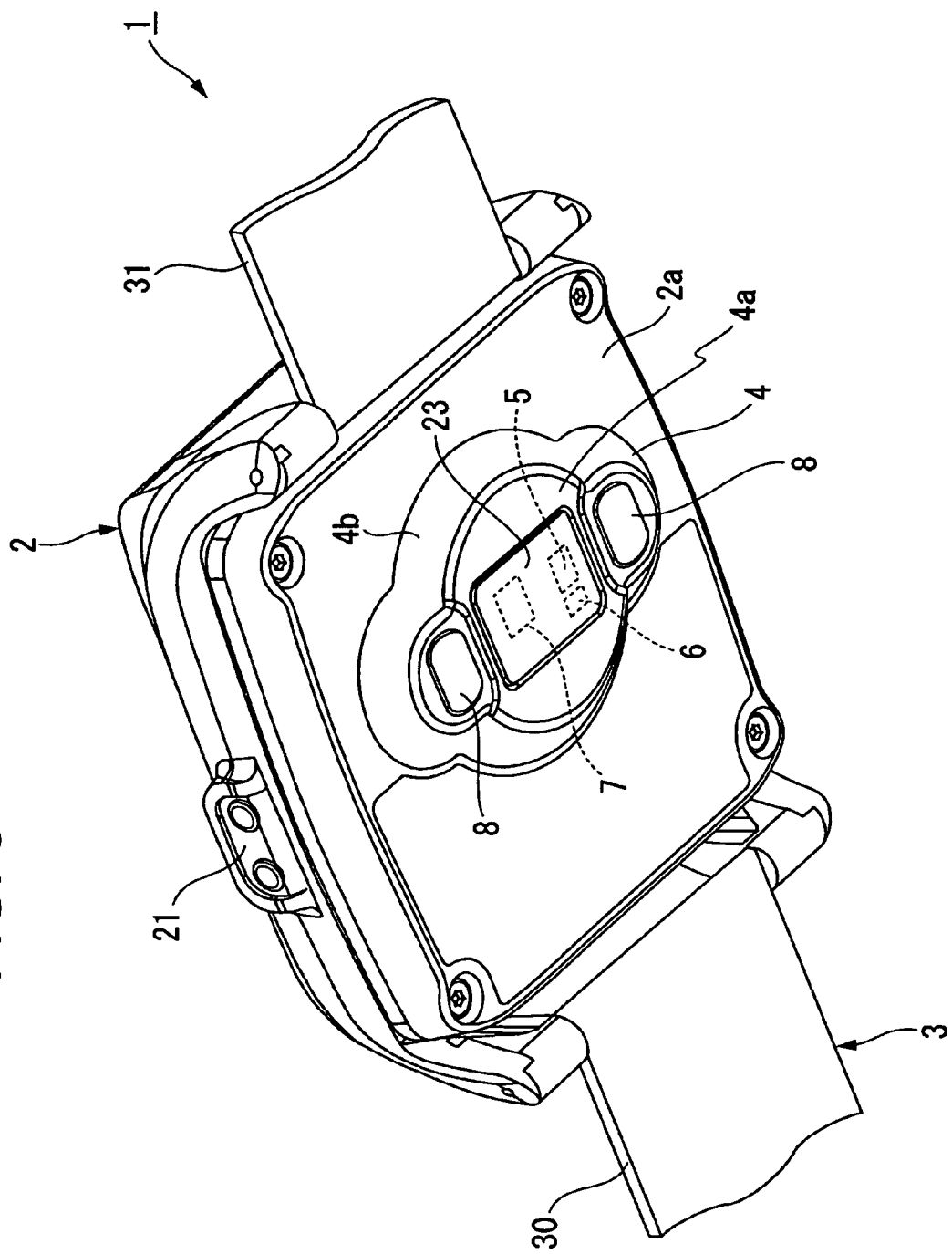
FIG. 6 is a perspective view showing the organism information measuring device shown in FIG. 1 under a state of being obliquely seen from below.
Figure 7:
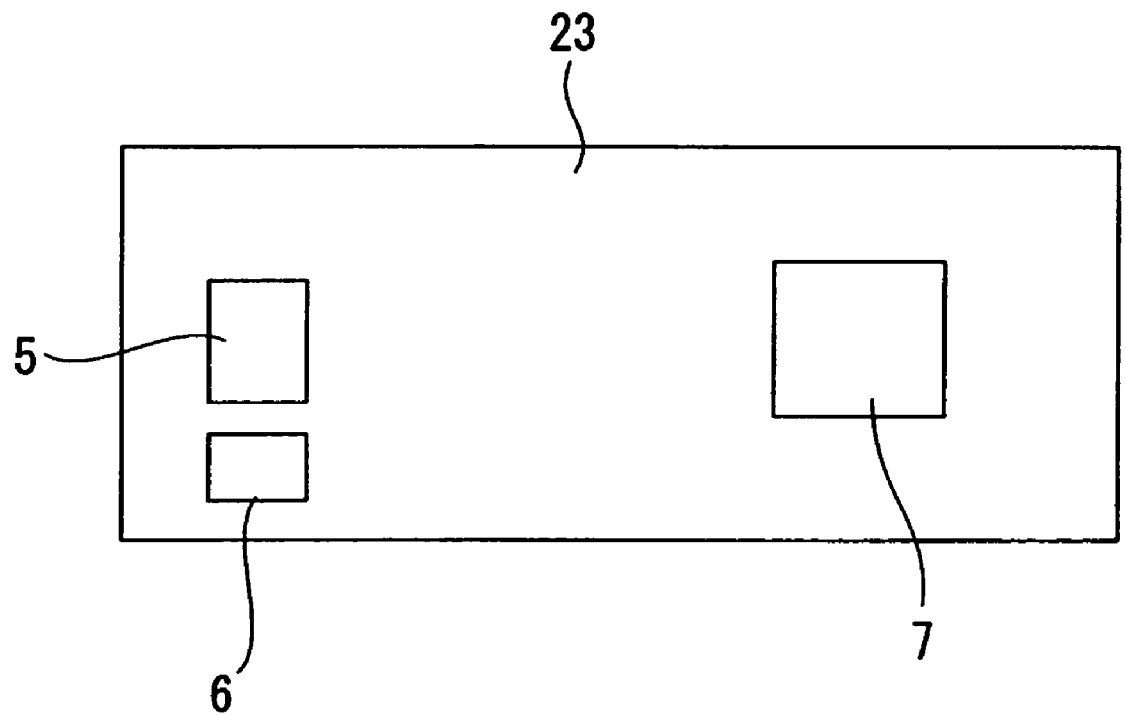
FIG. 7 is a view showing a positional relation between an LED and both PDs, as viewed from above a cover glass.

As shown in FIG. 6 and FIG. 7, in a lower face 4a of this protrusion part 4, i.e., the lower face 2a of the housing 2, there are disposed an LED (Light Emitting Diode) (light irradiating part) 5 which irradiates the light toward the organism under the state of contacting with the organism surface B, a 1st PD (Photo Diode) (1st light receiving part) 6 and a 2nd PD (2nd light receiving part) 7, each of which receives the backward scattered light from the organism within the light irradiated by the LED 5 and generates a pulse signal (organism information signal) complying with a received light quantity, and one pair of electrodes 8 which detect whether or not the above LED and both the PDs 6, 7 contact with the organism surface B. As the LED 5, there is used an LED whose wavelength is 530 nm for instance. As the 1st PD and the 2nd PD, there is used a PD whose sensitivity in long wavelength of wavelength 600 nm or longer for instance has been cut.

Further, in the housing 2, there is provided a data processing part (organism information operating part) 9 which calculates the pulse rate on the basis of the pulse signals generated by both the PDs 6, 7.

The above housing 2 comprises a plastic or a metal material such as aluminum, and is formed, e.g., in an approximately rectangular shape when seen from above while having a predetermined thickness. An approximately square shape cover glass 10 is fitted to a center portion of an upper face 2b of the housing 2 and, inside the cover glass 10, there is disposed a display part 11 which displays the above calculated pulse rate and other various information.

Figure 3:
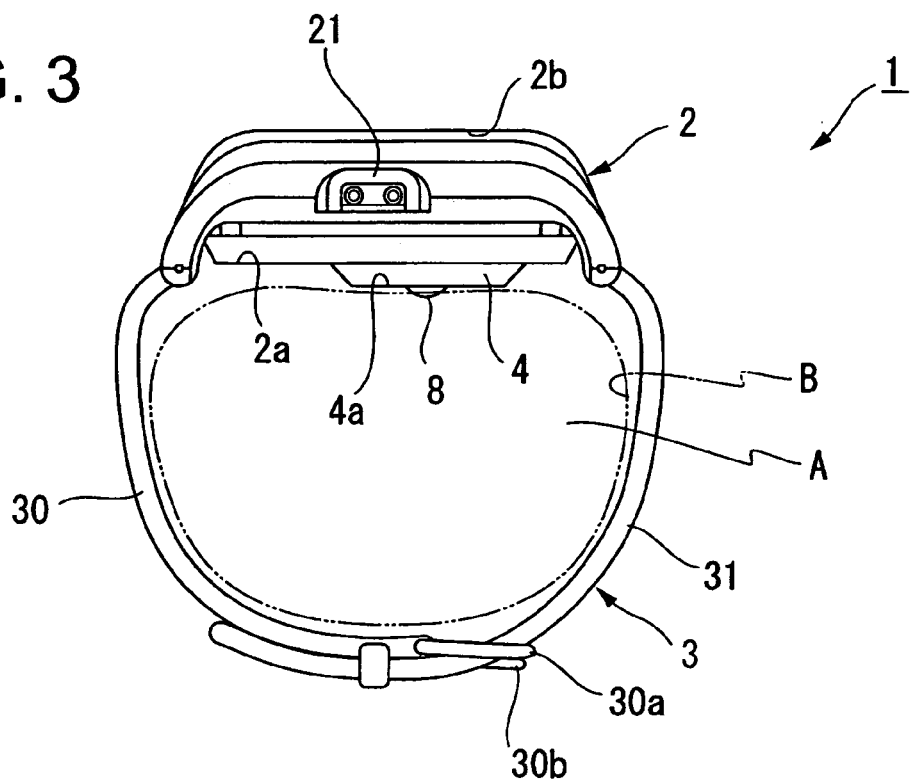
FIG. 3 is a side view showing the state that the organism information measuring device shown in FIG. 1 has been mounted to the wrist, and is a view seen from a direction opposite to a direction shown in FIG. 2.
Figure 4:
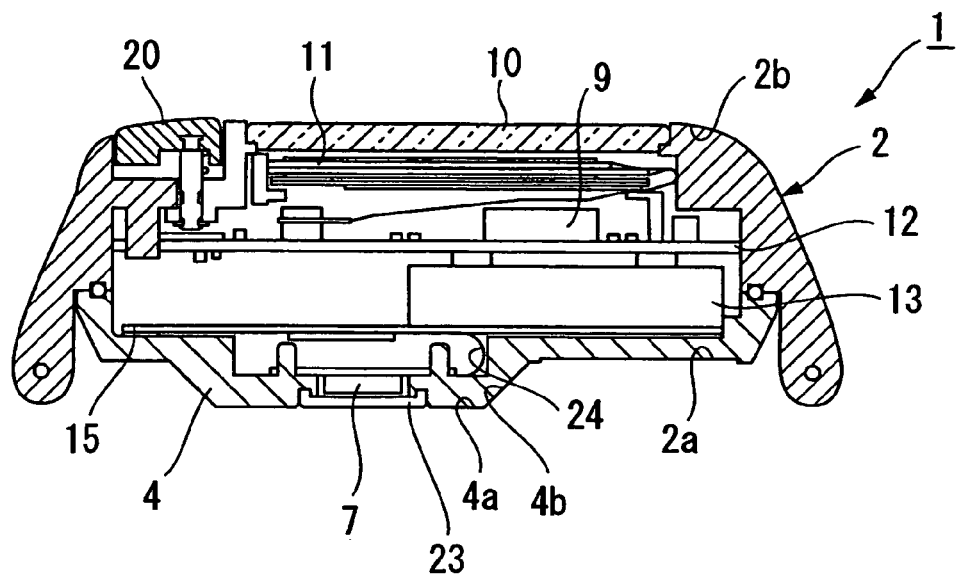
FIG. 4 is a sectional view of the organism information measuring device shown in FIG. 1, which is seen from an arrow line 4—4.
Figure 5:
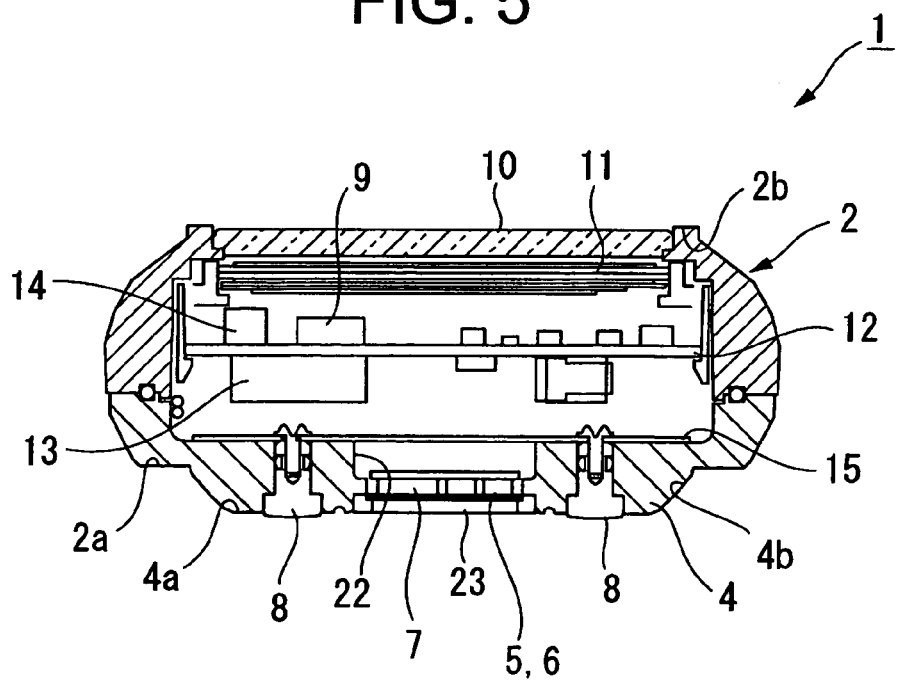
FIG. 5 is a sectional view of the organism information measuring device shown in FIG. 1, which is seen from an arrow line 5—5.

Further, as shown in FIGS. 3–5, in the housing 2, there is provided a main substrate 12 and, to the main substrate 12, there are mounted or electrically connected by a wiring, etc. the above data processing part 9, the above display part 11, a storage battery 13 capable of being charged, a memory 14 for recording the pulse rate, a sub-substrate 15, and other various electronic components.

The above data processing part 9 is one containing an IC component such as CPU, and is adapted such that, after the pulse signals generated by both PDs 6, 7 have been once amplified by an amplifier and the like, it performs a predetermined processing such as high-speed Fourier transformation processing (FFT processing) and calculates the pulse rate by comparing results of both processings. As to this calculation of the pulse rate, it is detailedly explained later.

Further, the data processing part 9 is adapted such that it records the calculated pulse rate to the memory 14 and displays it to the display part 11 on the basis of an input from each button 20 mentioned later. Additionally, the data processing part 9 has a function of synthetically controlling other constituent articles as well.

The above display part 11 is a liquid crystal display such as LCD (Liquid Crystal Display), and has a time display function which displays, besides the above-mentioned pulse rate, the current time counted by, e.g., a quartz oscillator not shown in the drawing, and a function of displaying other various information. It is adapted so as to be capable of displaying, e.g., the current time, a date, a day of week, a remaining electric power quantity of the storage battery 13, and the like.

Figure 2:
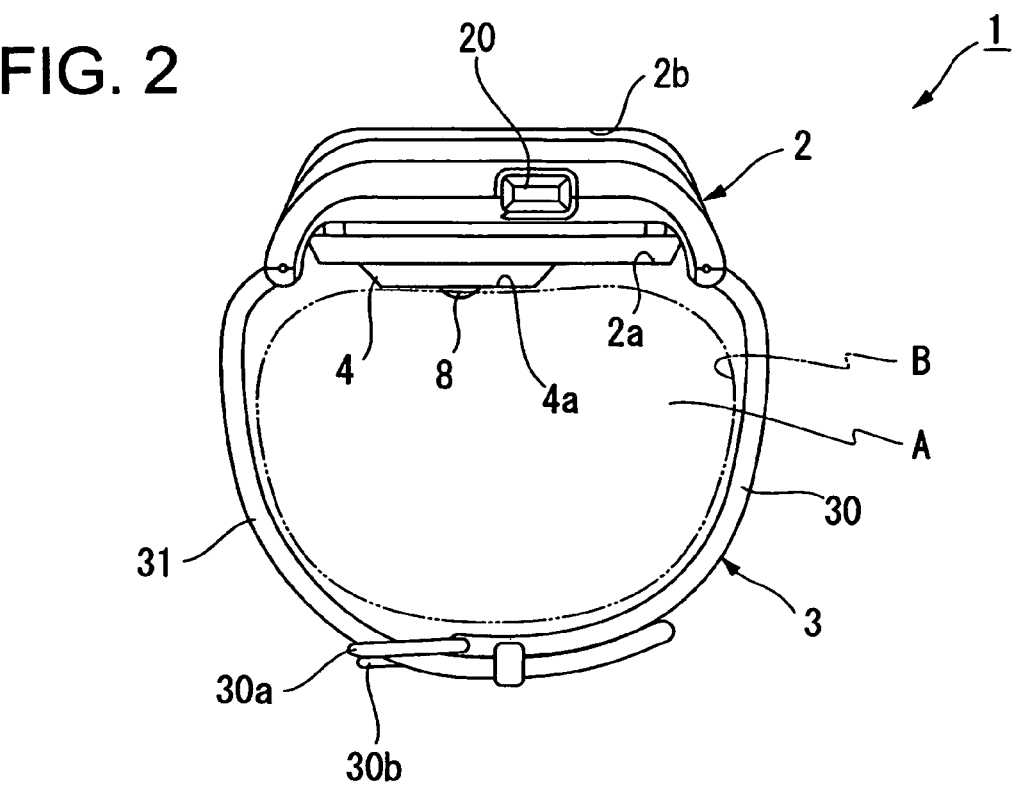
FIG. 2 is a side view showing a state that the organism information measuring device shown in FIG. 1 has been mounted to a wrist.

Further, as shown in FIG. 1 to FIG. 3, in the housing 2, there are provided plural buttons 20, for example, three buttons 20 existing in the upper face 2b of the housing 2 and disposed in an underside of the display part 11, and one button 20 disposed in a side face of the housing 2. It is adapted such that, by pressing down each of these buttons 20, various operations can be performed. It is adapted so as to be capable of performing such operations as, e.g., a measurement commencement of the pulse rate, a measurement stop, a display changeover between the pulse rate and the current time, and a data transmission of the pulse rate data recorded in the memory 14 to an external equipment.

Additionally, in the side face of the housing 2, there is provided an external connection terminal 21 for charging the above storage battery 13 by supplying an electric power from an outside such as battery charger. Incidentally, the external connection terminal 21 may be protected by attaching a cover etc. so as to cover the external connection terminal 21. By so doing, it becomes possible to protect the external connection terminal 21 from waterdrop, dust and the like, so that it is more appropriate. Further, not limited to the external connection terminal 21, it may be constituted such that a transformer and the like for respectively supplying the electric power are provided in the battery charger and the housing 2, and a charging of the storage battery 13 is performed under a non-contact state.

As shown in FIG. 6, the above protrusion part 4 is formed in a shape in which three circles have been combined in a shape, i.e., a keyhole-like shape in which, to a center circle, there have been connected two circles each having a diameter smaller than the former circle so as to interpose it from left and right.

As shown in FIG. 5, in a center of the lower face 4a of this protrusion part 4, there is formed a through-hole 22 causing an inside of the housing 2 to communicate with an outside, and a cover glass 23 is fixed to the housing 2 so as to close the through-hole 22 concerned. And, the above LED 5 and both the PDs 6, 7 are disposed so as to contact with an inside of the cover glass 23.

As shown in FIG. 6 and FIG. 7, out of both the PDs 6, 7, the 1st PD 6 is disposed near the LED 5, and the 2nd PD 7 is disposed in a position spaced from the LED 5 more than a distance between the 1st PD 6 and the LED 5. Further, the 2nd PD 7 has a light receiving area that is proportional to and increases in accordance with a distance spacing from the LED 5. In other words, the 2nd PD 7 is set such that the light receiving area is larger than the 1st PD 6.

It is adapted such that the pulse signals from both these PDs 6, 7 are sent to the above data processing part 9 through a flexible substrate 24, the sub-substrate 15 and the main substrate 12.

The above one pair of electrodes 8 are disposed in the lower face 4a of the protrusion part 4 under a state that the LED 5 and both the PDs 6, 7 have been interposed between them. That is, one pair of electrodes 8, the LED 5 and both the PD 6, 7 are disposed so as to be arranged in one row in a direction perpendicular to a longitudinal direction of the housing 2. Further, one pair of electrodes 8 are provided such that their tips somewhat protrude from the lower face 4*a* of the protrusion part 4, and their base end sides are electrically connected to the sub-substrate 15.

These one pair of electrodes 8 have a function of detecting, on the basis of a potential difference between the electrodes, whether or not they contact with the organism surface B. The data processing part 9 is set so as to control, when this detected result has been received and it has been detected that they contact with the organism surface B for instance, an operation of the LED 5 such that the light is irradiated from the LED 5. Incidentally, not limited only to this case, it may be set such that, when the fact has been detected that they don't contact with the organism surface B for instance, the FFT processing is not performed.

As shown in FIG. 1, the above fixing means 3 has a 1st band 30 and a 2nd band 31, whose base end sides are attached to the housing 2 and which can be mounted to the wrist A. The 1st band 30 and the 2nd band 31 are provided in the longitudinal direction of the housing 2 so as to be opposed while interposing the housing 2.

A buckle 30*a* and a tongue 30*b* are attached to the above 1st band 30 in its tip. Further, in the 2nd band 31, there are formed plural insertion holes 31*a* into which the above tongue 30*b* is inserted along the longitudinal direction of the 2nd band 31 concerned. By this, it is adapted such that lengths of the 1st band 30 and the 2nd band 31 can be adjusted in compliance with a thickness of the wrist A of a user.

It is explained hereunder about an organism information measuring method in which the pulse rate is calculated by the organism information measuring device 1 constituted like this under the state of being attached to the wrist A.

The organism information measuring method of the present embodiment has a transformation process in which, from the backward scattered light received by the 1st PD 6 and the 2nd PD 7, pulse signals complying with the received light quantity are respectively generated and the pulse signals concerned are FFT-processed, and an operation process in which values transformed by the transformation process concerned are normalized by a power spectrum of optional frequency and the pulse information is operated by mutually subtracting the normalized values. It is detailedly explained below about each of these processes.

First, as shown in FIG. 2 and FIG. 3, both the bands 30, 31 are wound so as to encircle the wrist A of the user, and the tongue 30*b* of the 1st band 30 is inserted into the insertion hole 31*a* of the 2nd band 31 in compliance with a size of the wrist A, thereby mounting the housing 2 to the wrist A. When the housing 2 is mounted to the wrist A, since the protrusion part 4 protrudes than the lower face 2*a* of the housing 2, the organism surface B and the lower face 4*a* of the protrusion part 4 become a closely contacted state. Accordingly, it is unnecessary to mount the housing 2 so as to fasten the wrist A, and it suffices to adjust the lengths of both the bands 30, 31 such that they are tightened by a predetermined force.

If the organism surface B and the lower face 4*a* of the protrusion part 4 come into a closely contacted state, i.e., when the organism surface B contacts with the lower face 4*a* of the protrusion part 4, one pair of electrodes 8 contact with the organism surface B. Especially, since one pair of electrodes 8 are disposed so as to somewhat protrude from the lower face 4*a* of the protrusion part 4, they are liable to contact with the organism surface B. If one pair of electrodes 8 contact with the organism surface B, a discharge is performed through the organism surface B, so that a voltage between both the electrodes 8 decreases. By receiving this voltage drop (for example, a drop to lower than a certain threshold value), the data processing part 9 performs a detection of the fact that one pair of electrodes 8 are surely contacting with the organism surface B. That is, the fact is detected that the LED 5 and both the PDs 6, 7 are surely contacting with the organism surface B. Especially, since one pair of electrodes 8 are disposed with the LED 5 and both the PDs 6, 7 being interposed between them, it is possible to accurately detect whether or not the LED 5 and both the PDs 6, 7 are contacting with the organism surface B.

If the fact is detected that the LED 5 and both the PDs 6, 7 are contacting with the organism surface B, the data processing part 9 irradiates the light from the LED 5 toward the organism. The irradiated light is absorbed and scattered in the organism by the tissues, such as fat and muscle, and the blood, and one part of the irradiated light is received by both the PDs 6, 7 as the backward scattered light. This received light fluctuates with the change in blood quantity by the pulsation. Both the PDs 6, 7 receive this backward scattered light and generate the pulse signal complying with the change in the received light quantity, thereby outputting it to the data processing part 9. In other words, since a light quantity of the backward scattered light of the light irradiated from the LED 5 fluctuates in compliance with a blood flow fluctuation in an artery and an arteriole inside the wrist A, both the PDs 6, 7 can perform a reception of the pulsation of the artery, i.e., the backward scattered light complying with a pulse wave. By this, both the PDs 6, 7 can perform a generation of the pulse signal.

On this occasion, since the 1st PD 6 is disposed near the LED 5, it receives the light depending on the LED 5 more than the backward scattered light from the organism. That is, it receives much light containing no pulse signal, e.g., the light directly entering from the LED 5, the light reflected by the organism surface B, and the light reflected by the cover glass 23. On the other hand, since the 2nd PD 7 is disposed in the position spaced from the LED 5, it receives much backward scattered light from the organism in addition to the light depending on the LED 5.

The data processing part 9 performs the FFT processing after amplifying the pulse signal sent from both the PDs 6, 7. That is, the process till this FFT processing is the above transformation process.

Figure 8:
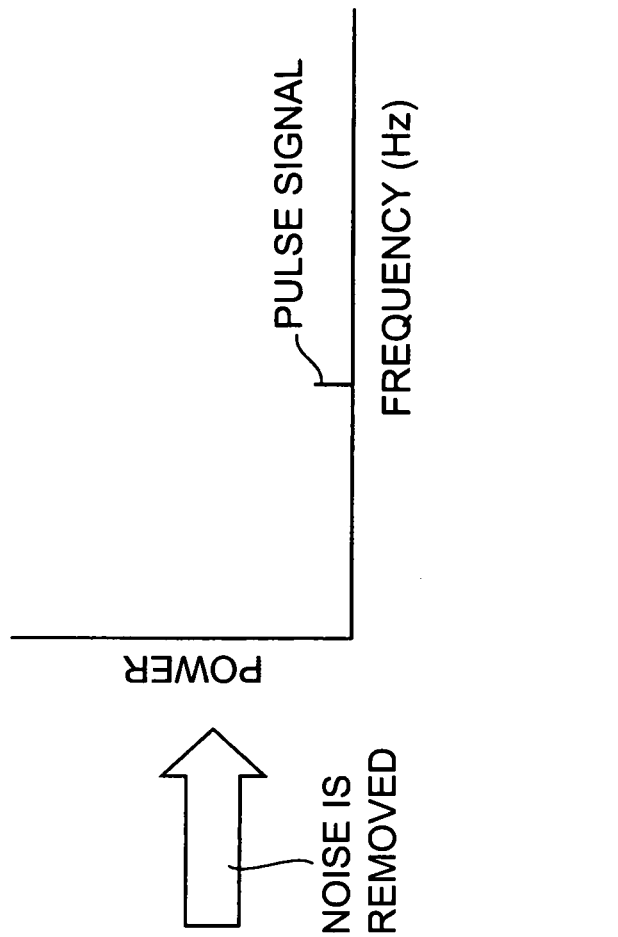
FIG. 8 is a diagram showing a state that a data processing part has calculated a pulse rate on the basis of pulse signals generated by a 1st PD and a 2nd PD.

After the transformation process, the operation process is performed. In other words, the data processing part 9 can accurately detect only the pulse signal by normalizing the FFT-processed values by the power spectrum of optional frequency and mutually subtracting the normalized values (mutual FFT results), i.e., as shown in FIG. 8, removing (subtracting) the pulse signal generated by the 1st PD 6 from the pulse signal generated by the 2nd PD7. By performing this operation process, it is possible to remove as far as possible the noise (electrical disturbance) containing no organism information from the pulse signal generated by the 2nd PD 7. Accordingly, it is possible to improve in S/N ratio, and it is possible to perform the more accurate calculation of the pulse rate.

And, the data processing part 9 records the calculated pulse rate to the memory 14 and displays it to the display part 11 on the basis of each button 20 operation.

Further, since the 2nd PD 7 is set such that its light receiving area is larger than the 1st PD 6, even if it is spaced from the LED 5, it can receive the light depending on the LED 5 with the light quantity of the same degree as the PD 6 and receives much backward scattered light from the organism. By this, since the removal of the noise can be more surely performed and the pulse signal can be received in greater quantity, it is possible to more accurately perform the detection of the pulse rate.

Further, by pressing down each button 20 at a necessary time, since the user can easily perform a confirmation by displaying the detected pulse rate to the display part 11, it is simple as to a use. Further, by the operation of each button 20, since the user can confirm also information other than the pulse rate, for example, the time instant, the remaining electric power of the storage battery 13 and the like, by the display part 11, it is easy to use.

Further, as mentioned above, since the housing 2 is mounted to the wrist A by being fastened by both the bands 30, 31 with a predetermined force, the user does not feel a sense of oppression even if it is mounted for a long time, and thus does not feel uncomfortably.

Further, in a case where the electric power is charged to the storage battery 13, the charging can be performed by connecting a charging cord etc. connected to the battery charger to the external connection terminal 21, so that it is unnecessary to separately prepare a usual battery. Accordingly, it is possible to reduce maintenance expenses. Incidentally, it may be constituted such that, by providing sound outputting means such as a buzzer which outputs a sound in the housing 2, a charging time (charging timing) may be informed by outputting the sound in a case where a charged quantity of the storage battery 13 has reduced till approaching "0".

As explained above, according to the organism information measuring device 1 of the present embodiment, by the fact that the data processing part 9 takes the pulse signal generated by the 1st PD 6 into consideration, it is possible to remove as far as possible the noise (electrical disturbance) containing no organism information from the pulse signal generated by the 2nd PD 7. Accordingly, it is possible to improve S/N ratio, and it is possible to perform more accurate calculation of the organism information.

Incidentally, a technical scope of the present invention is not limited to the above embodiment, and it is possible to add various modifications within a scope not deviating from a gist of the present invention.

For example, in the above embodiment, although it has been explained with the pulse rate as an example of the organism information, it may be any organism information, not limited to the pulse rate, that is indicative of a condition of the organism.

Further, although it has been made the constitution in which the 1st PD provided near the LED is one piece, it may be made a constitution in which the 1st PD comprises plural pieces or PDs. In this case, it suffices if the data processing part is set such that any one or an average value of the pulse signals generated by the plural 1st PDs is utilized. By so doing, since the noise containing no organism information can be surely received irrespective of a position where the 1st PD is provided, it is possible to more accurately perform the calculation of the pulse rate.

Further, to the housing, there may be added a function, such as radio communication means capable of radio-communicating between it and other electronic equipment. By so doing, by such a radio communication as Bluetooth, it is possible to data-transmit the pulse rate recorded in the memory to the external electronic equipment, or input various information to the memory.

Additionally, in the above embodiment although the LED 5 has been made one, the invention is not limited to this and the LED may be constituted as shown in FIG. 9 such that a 1st LED 5a (1st light irradiating part) for detecting the organism information, each of which irradiates light of different wavelength, are provided and, out of both the LEDs, the 1st LED 5a utilizes a light whose wavelength is short relative to that of the 2nd LED and the 2nd LED 5b utilizes a light whose wavelength is long relative to that of the 2st LED. As the 1st LED 5a there is used an LED in which the wavelength is 470 nm for instance, and as the 2nd LED 5b there is used an LED in which the wavelength is 530 nm for instance.

By so doing, the 1st PD receives more light containing no organism information (noise component is much), and the 2nd PD receives more backward scattered light from the organism. Accordingly, it is possible to further improve the S/N ratio, so that it is possible to perform the more accurate calculation of the organism information. Especially, since the 2nd LED utilizes the light whose wavelength is long, it is easy to obtain the backward scattered light from the organism.

Further, on this occasion, it is desirable that the above 2nd LED is provided at a distance in which the light irradiated from the 1st LED does not directly enter. By so doing, the 2nd PD can collectively receive the backward scattered light without undergoing an influence from the 1st LED, so that it is possible to accurately calculate the organism information.

According to the organism information measuring device and the organism information measuring method, which concern the present invention, it is possible to remove as far as possible the light containing no organism information, i.e., noise (electrical disturbance), from the organism information signal generated by the 2nd light receiving part. By this, it is possible to improve S/N ratio, and it is possible to perform the more accurate calculation of the organism information.

What is claimed is:

1. An organism information measuring device comprising:
    a main body having a lower face that is disposable in contact with an organism surface of an organism during use of the device;
    a first light irradiating part disposed in the lower face of the main body for irradiating light toward the organism, the light having a relatively short wavelength for primarily detecting noise;
    a second light irradiating part disposed in the lower face of the main body for irradiating light toward the organism, the light having a relatively long wavelength for primarily detecting organism information;
    a first light receiving part disposed in the lower face of the main body for receiving light including backward scattered light originating from the first and second light irradiating parts and producing organism information signals according to the quantity of received light;
    a second light receiving part disposed in the lower face of the main body for receiving light including backward scattered light originating from the first and second light irradiating parts and producing organism information signals according to the quantity of received light, the second light receiving part being located farther from the first and second light irradiating parts than the first light receiving part; and
    a data processing part disposed in the main body for determining organism information indicative of an organism condition on the basis of the organism information signals produced by the first and second light receiving parts.

2. An organism information measuring device according to claim 1; wherein the second light receiving part is disposed a sufficient distance from the first light irradiating part so that light irradiated by the first light irradiating part does not directly enter the second light receiving part.

3. An organism information measuring device according to claim 1; wherein the first and second light irradiating parts and the first and second light receiving parts are disposed in an opening in the lower face of the main body.

4. An organism information measuring device according to claim 1; wherein the relatively short wavelength of light irradiated by the first light irradiating part has a wavelength of 470 nm and the relatively long wavelength of light irradiated by the second light irradiating part has a wavelength of 530 nm.

5. An organism information measuring device according to claim 1; wherein the organism information determined by the data processing part is pulse rate.

6. An organism information measuring device comprising:
    a main body having a lower face that is disposable in contact with an organism surface of an organism during use of the device;
    a light irradiating part disposed in the lower face of the main body for irradiating light toward the organism;
    a first light receiving part disposed in the lower face of the main body for receiving light including backward scattered light originating from the light irradiating part and producing an organism information signal according to the quantity of received light;
    a second light receiving part disposed in the lower face of the main body for receiving light including backward scattered light originating from the light irradiating part and producing an organism information signal according to the quantity of received light, the second light receiving part being located a farther distance from the light irradiating part than the first light receiving part, and the second light receiving part having a light receiving area having a size proportional to the distance of the second light receiving part from the light irradiating part; and
    a data processing part disposed in the main body for determining organism information indicative of an organism condition on the basis of the organism information signals produced by the first and second light receiving parts.

7. An organism information measuring device according to claim 6; wherein the second light receiving part is disposed a sufficient distance from the light irradiating part so that light irradiated by the light irradiating part does not directly enter the second light receiving part.

8. An organism information measuring device according to claim 6; wherein the light receiving area of the second light receiving part is larger than that of the first light receiving part.

9. An organism information measuring method comprising the steps of:
    irradiating light by a first light irradiating part toward an organism, the light having a relatively short wavelength for primarily detecting noise;
    irradiating light by a second light irradiating part toward the organism, the light having a relatively long wavelength for primarily detecting organism information;
    receiving backward scattered light from the organism by a first light receiving part located near the first and second light irradiating parts and by a second light receiving part located farther from the first and second light irradiating parts than the first light receiving part; and
    determining organism information indicative of an organism condition on the basis of the backward scattered light received by the first and second light receiving parts.

10. An organism information measuring method according to claim 9; wherein the relatively short wavelength of light irradiated by the first light irradiating part has a wavelength of 470 nm and the relatively long wavelength of light irradiating by the second light irradiating part has a wavelength of 530 nm.

11. An organism information measuring method according to claim 9; wherein the organism information is pulse rate.

* * * * *